(12) United States Patent
Bille

(10) Patent No.: US 6,610,050 B2
(45) Date of Patent: Aug. 26, 2003

(54) LASER BEAM DELIVERY SYSTEM WITH MULTIPLE FOCAL POINTS

(75) Inventor: Josef Bille, Heidelberg (DE)

(73) Assignee: 20/10 Perfect Vision, Optische Geraete GmbH, Heidelberg (DE)

( * ) Notice: Subject to any disclaimer, the term of this patent is extended or adjusted under 35 U.S.C. 154(b) by 0 days.

(21) Appl. No.: 09/919,627

(22) Filed: Jul. 27, 2001

(65) Prior Publication Data

US 2003/0023231 A1 Jan. 30, 2003

(51) Int. Cl.[7] ................................................ A61F 9/008
(52) U.S. Cl. ................................ 606/5; 606/4; 128/898
(58) Field of Search ........................... 606/4–5; 128/898

(56) References Cited

U.S. PATENT DOCUMENTS

| | | | |
|---|---|---|---|
| 4,727,381 A | | 2/1988 | Bille et al. |
| 4,884,884 A | * | 12/1989 | Reis ................... 606/5 |
| 4,887,019 A | * | 12/1989 | Reis et al. ............ 606/4 |
| 4,887,592 A | | 12/1989 | Loertscher |
| 4,907,586 A | * | 3/1990 | Bille et al. ............ 606/5 |
| 4,988,348 A | | 1/1991 | Bille |
| 5,062,702 A | | 11/1991 | Bille |
| 5,480,396 A | * | 1/1996 | Simon et al. ......... 606/4 |
| 5,624,437 A | * | 4/1997 | Freeman et al. ...... 606/5 |
| 5,865,830 A | * | 2/1999 | Parel et al. .......... 606/5 |
| 5,920,373 A | | 7/1999 | Bille |
| 5,993,438 A | * | 11/1999 | Juhasz et al. ........ 606/5 |
| 6,050,687 A | | 4/2000 | Bille et al. |
| 6,110,166 A | * | 8/2000 | Juhasz ................. 606/5 |
| 6,210,399 B1 | | 4/2001 | Parel |
| 6,331,177 B1 | * | 12/2001 | Munnerlyn et al. ... 606/5 |

FOREIGN PATENT DOCUMENTS

| | | |
|---|---|---|
| WO | WO 94/03134 | 2/1994 |
| WO | WO 99/53992 | 10/1999 |

* cited by examiner

*Primary Examiner*—Linda C. M. Dvorak
*Assistant Examiner*—Henry M. Johnson, III
(74) *Attorney, Agent, or Firm*—Nydegger & Associates

(57) ABSTRACT

An optical system for partitioning and focusing a laser beam into a plurality of focal points to simultaneously photoalter corneal tissue at a plurality of locations includes a laser source. In one embodiment, an active mirror is used to partition the master beam into diverging beams. In another embodiment, a lenslet array in combination with a field lens is used to partition the master beam into seven diverging beams. The resultant diverging beams are then collimated, magnified and focused into a plurality of focal points using a set of optical lenses. Each focal point has an average pulse energy of approximately 5 $\mu J$ rendering it suitable for subsurface photoalteration of corneal tissue. A scanning mechanism is provided to move the plurality of focal points, as a group, along a predetermined path through the cornea to quickly and safely photoalter a predetermined volume of subsurface corneal tissue.

17 Claims, 2 Drawing Sheets

LASER BEAM DELIVERY SYSTEM WITH MULTIPLE FOCAL POINTS

FIELD OF THE INVENTION

The present invention pertains generally to laser systems. More particularly, the present invention pertains to laser beam delivery systems for simultaneously creating a plurality of focal points from a single laser source. The present invention is particularly, but not exclusively, useful for creating a plurality of laser focal points suitable for performing refractive surgery.

BACKGROUND OF THE INVENTION

In a conventional LASIK procedure, a corneal flap is first created with a microkeratome. Next, the flap is lifted to expose stromal tissue. Once exposed, the stromal tissue is photoablated using an Excimer laser. After photoablation, the flap is replaced over the cornea and the cornea is allowed to heal. The result is a reshaped cornea. By reshaping the cornea in this manner, vision deficiencies in the patient can be corrected. There are, however, several drawbacks associated with using a microkeratome to create the flap. For one, using a microkeratome is labor intensive. Additionally, the results obtained when using a microkeratome are highly dependent on the skill of the surgeon. Finally, shape of the exposed bed of stromal tissue that results from the use of a microkeratome is generally limited to flat surfaces. Because of these drawbacks, the development of new techniques for creating corneal flaps is merited.

One technique for creating a corneal flap that is gaining widespread acceptance involves the use of a pulsed laser beam to photoalter stromal tissue. In this technique, a pulsed laser is focused beneath the anterior surface of the cornea to a focal point within the stroma. For example, a pulsed laser beam having a pulse frequency of approximately 4 kHz with pulse durations as long as a few nanoseconds or as short as only a few femtoseconds can be used for subsurface photoalteration of stromal tissue. For a commonly used focal point size of approximately 10 $\mu$m in diameter, a typical laser source can produce an average pulse energy of approximately 60 $\mu$J at the focal point. This energy (60 $\mu$J) is far in excess of the energy required to photoalter stromal tissue. Specifically, only about 2 $\mu$J is required for photoalteration of stromal tissue, with about 5 $\mu$J being optimal. Consequently, when only a single focal point is used, most of the energy available in a typical pulsed laser source is wasted.

Consider now an exemplary flap for a LASIK procedure having a diameter of approximately 10 mm. For this flap, the photoalteration of approximately 200,000 stromal points is required. Stated another way, approximately 200,000 pulses, with each pulse having an average energy of approximately 5 $\mu$J, are required. Continuing with this example, for a 4 kHz laser using a single focal point, about 50 seconds would be required to create a 10 mm flap. It is to be appreciated that procedures requiring this length of time (i.e. 50 seconds), pose a number of serious problems. One problem with lengthy procedures is eye movement. To overcome eye movement, eye restraint is often used. Unfortunately, restraining the eye for long periods of time can cause discomfort for the patient. Another problem associated with long procedure times involves patient blinking. Each time a patient blinks, a new tear film is deposited on the anterior surface of the cornea. Each tear film affects the optical path of the laser beam in a slightly different manner, affecting the precision of the operation. Thus, it is preferable to perform an entire procedure with a single tear film, if possible. Typically, 10 seconds is about the maximum time that a patient can restrain from blinking, thus it is preferable to complete an entire procedure in less than about 10 seconds.

In all surgical procedures, damage to non-target (i.e. collateral) tissue is to be avoided. During photoalteration of target tissue, nearby (non-target) tissue is heated. Some heating of non-target tissue can be accommodated without damage to the non-target tissue. Specifically, for stromal tissue, a temperature rise of about 3° C. can be tolerated without long-term cell damage. In contrast, temperature increases of between about 8° C. and 23° C. can result in tissue shrinkage, cell denaturation, loss of cell function and coagulation. Importantly for the present invention, when multiple focal points are used to simultaneously photoalter tissue, a minimum spacing between adjacent focal points is required to prevent damage to non-target tissue from the heat generated during photoalteration.

In light of the above, it is an object of the present invention to provide a laser system suitable for the purposes of expeditiously photoaltering stromal tissue without heating collateral tissue to harmful temperatures. It is another object of the present invention to provide a pulsed laser system capable of generating a plurality of spaced apart laser focal points, with each focal point having a suitable pulse energy to accomplish photoalteration of stromal tissue. It is yet another object of the present invention to provide a laser system that partitions a pulsed laser beam into a plurality of laser focal points having adequate spacing between focal points to allow the heat generated during photoalteration to dissipate, thereby preventing heat damage to non-target tissue. Still another object of the present invention is to provide a multiple focal point pulsed laser system capable of photoaltering approximately 200,000 points within the stroma in less than approximately 10 seconds. It is still another object of the present invention to provide a multiple focal point, pulsed laser system capable of expeditiously photoaltering an entire 10 mm corneal flap during the period between the blinks of the patient (i.e. in less than approximately 10 seconds). Yet another object of the present invention is to provide a laser system and a method for its use which are relatively easy to use, simple to implement, and comparatively cost effective.

SUMMARY OF THE PREFERRED EMBODIMENTS

The present invention is directed to an optical system for partitioning and focusing a laser beam onto a plurality of focal points to simultaneously photoalter corneal tissue at a plurality of locations. The plurality of focal points can be scanned, as a group, through the cornea to quickly and safely photoalter a predetermined volume of subsurface corneal tissue. For the present invention, the system includes a laser source capable of generating a pulsed laser beam (hereinafter referred to as a master beam) having a pulse frequency of approximately 4 kHz and an average pulse energy of approximately 60 $\mu$J.

In one embodiment for the present invention, the master beam produced by the laser source is directed into a lenslet array to partition the master beam into a plurality of beams. Preferably, the lenslet array has six lenslets arranged in a circle surrounding a center lenslet. Thus, seven spaced apart beams emerge from the lenslet array. From the lenslet array, the seven beams are directed into a series of optical lenses and a scanner. In detail, the seven beams are first directed into a field lens to diverge the seven beams. From the field lens, the diverging beams are directed to a collimating lens to place the seven beams onto parallel beam paths. Next, the collimated beams are directed to a pair of relay lenses arranged as a telescope to magnify the collimated beams.

Once magnified, the beams are directed to a cutting lens to focus each of the beams to a separate focal point. Thus, a group (or cluster) of focal points is established. Like the lenslet array, the cluster of focal points is preferably arranged with six focal points distributed uniformly around a circle with the seventh focal point positioned at the center of the circle. For the present invention, a scanner is provided to move the cluster of focal points, as a group, through the cornea. Preferably, the scanner is interposed between the relay lenses that magnify the collimated beams.

In another embodiment for the present invention, an active mirror having approximately 40,000 active facets can be used to partition the master beam into seven diverging beams. The diverging beams from the active mirror are then collimated, magnified and focused using the optics described above. For both embodiments, a plurality of focal points suitable for subsurface photoalteration of corneal tissue is obtained, with each focal point having an average pulse energy of approximately 5 $\mu$J.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENT

Figure 1:
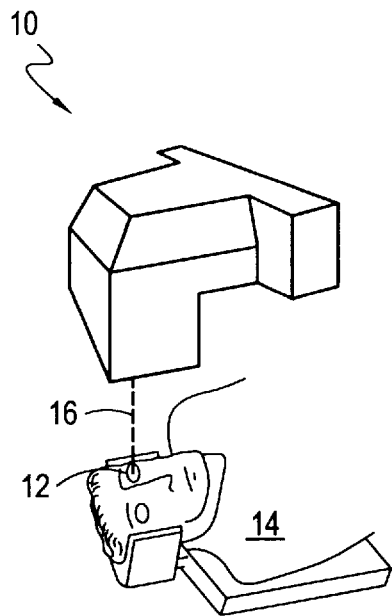
FIG. 1 is a perspective view of a patient being treated with a pulsed laser in accordance with the method of the present invention.

Referring initially to FIG. 1, a laser system 10 is shown for conducting a laser procedure on the eye 12 of a patient 14. As shown, the eye 12 of the patient 14 is aligned to receive a plurality of pulsed laser beams from the laser system 10. As detailed further below, a plurality of pulsed laser beams that are preferably centered substantially along axis 16 are simultaneously focused by the laser system 10 to focal points within the eye 12 of the patient 14 to photoalter stromal tissue. In accordance with the present invention, the photoalteration can be performed to create a flap suitable for a LASIK type procedure, to effect a refractive change in the cornea, to create a passageway or drainage channel in the eye 12, or to effect any other type of surgical procedure, in whole or in part, known in the pertinent art that requires either the incision or removal of ocular tissue.

Figure 2:
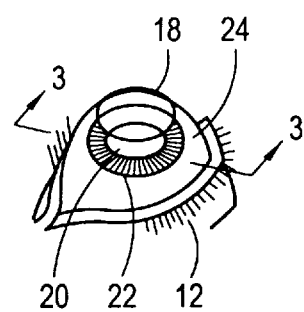
FIG. 2 is a perspective view of an eye.
Figure 3:
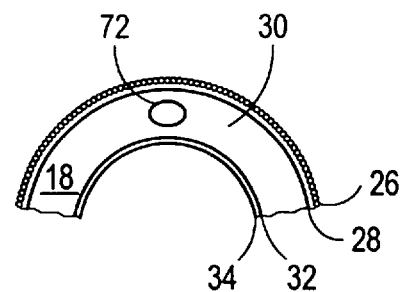
FIG. 3 is a cross sectional view of a portion of the cornea of the eye as seen along the line 3—3 in FIG. 2 showing the anatomical layers of the cornea and an exemplary volume of stromal tissue that can be removed in accordance with the methods of the present invention to effect a refractive change in the cornea.

FIG. 2 shows the anatomical structure of the human eye 12 including the cornea 18, the pupil 20, the iris 22, and the sclera 24. In FIG. 3 it can be seen that the cornea 18 includes five anatomically definable layers of tissue. Going in a direction from anterior to posterior in FIG. 3, the tissue layers of the cornea 18 are: the epithelium 26, Bowman's membrane 28, the stroma 30, Decemet's membrane 32 and the endothelium 34. Of these, the stroma 30 is the thickest layer and contains the stromal tissue that is of general importance for the present invention. Specifically, the removal or destruction of stromal tissue is recognized as an effective way to reshape the cornea 18 and thereby effect a refractive change to the cornea 18. Additionally, creation of a flap suitable for use in a typical LASIK procedure requires the incision of stromal tissue.

Figure 4:
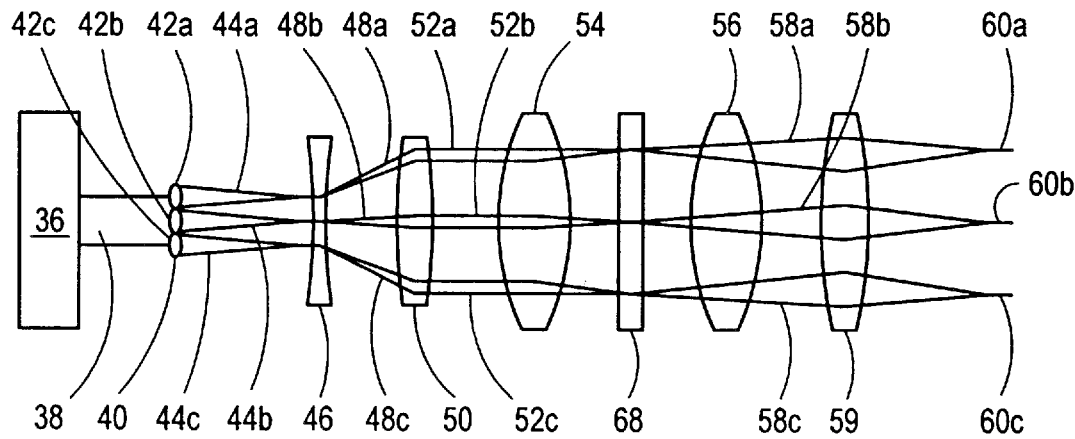
FIG. 4 is a schematic diagram of a laser system in accordance with the present invention having a lenslet array and a field lens to produce a plurality of diverging beams.

Referring now to FIG. 4, an embodiment of a laser system 10 is shown. As shown, the laser system 10 includes a laser source 36 for producing a pulsed laser beam 38. For purposes of the present invention, a pulsed laser beam 38 preferably has physical characteristics similar to those of the pulsed laser beams generated by a pulsed laser source as generally disclosed and claimed in U.S. Pat. No. 4,764,930, which issued to Josef F. Bille et al. for an invention entitled "Multiwavelength Laser Source." Furthermore, the present invention contemplates the use of a pulsed laser beam 38 having a pulse frequency of approximately 4 kHz with pulse durations as long as a few nanoseconds or as short as only a few femtoseconds. Preferably, the pulsed laser beam 38 has pulses with durations between approximately ten femtoseconds and five picoseconds (10 fsec–5 psec), and a wavelength longer than approximately nine hundred nanometers (900 nm). Also, the pulsed laser beam 38 preferably has a fluence of less than one hundred joules per square centimeter (<100 J/cm$^2$). With these characteristics, the pulsed laser beam can be focused to a focal point having a diameter of approximately ten micrometers (10 $\mu$m) that has an average pulse energy of approximately sixty microjoules (60 $\mu$J).

Figure 5:
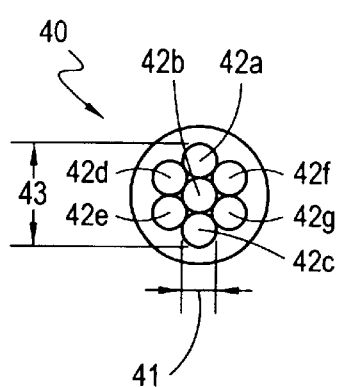
FIG. 5 is an elevational view of a lenslet array for use in the present invention.

Referring now with cross reference to FIGS. 4 and 5, it can be seen that the laser beam 38 produced by the laser source 36 is directed into a lenslet array 40 having seven lenslets 42a–g. It is to be appreciated that the seven lenslets 42a–g partition the laser beam 38 into seven spaced apart beams, three of which (i.e. beams 44a–c) are shown in FIG. 4. As shown in FIG. 5, the lenslet array 40 is preferably constructed having six lenslets 42a–f arranged about a circle surrounding a center lenslet 42g. Preferably, the lenslets 42a–f have a diameter 41 of approximately two millimeters (2 mm), and are close packed, as shown, within a circle having a diameter 43 of approximately six millimeters (6 mm). From the lenslet array 40, the beams 44a–c are first directed into a negative field lens 46 to diverge the beams 44a–c, thereby creating diverging beams 48a–c. From the field lens 46, the diverging beams 48a–c are directed to a collimating lens 50 to place the seven beams onto parallel beam paths. Next, the collimated beams 52a–c are directed through relay lens 54 and relay lens 56 for magnification. As shown, the relay lenses 54, 56 are arranged as a telescope to magnify the collimated beams 52a–c. Preferably, the relay lenses 54, 56 are configured to magnify the collimated beams 52 a–c at a magnification of approximately 8:1.

Figure 6:
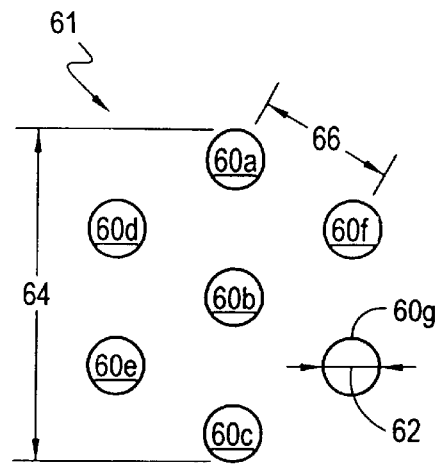
FIG. 6 is a diagram showing the preferred arrangement of focal points for the laser system of the present invention.

Referring still to FIG. 4, it can be seen that after passing through the relay lenses 54, 56, the magnified beams 58a–c are directed to a focusing lens 59 (i.e. a cutting lens) to focus each of the magnified beams 58a–c to a separate focal point 60a–c. With cross-reference now to FIGS. 4 and 6, it can be seen that a cluster 61 of seven focal points 60a–g is established. Like the lenslet array 40 (shown in FIG. 5), the cluster 61 of focal points 60a–g is preferably arranged with six focal points (60a and 60c–g) distributed uniformly around a circle with the seventh focal point 60b positioned at the center of the circle. Preferably, focal points 60a–g having a diameter 62 of approximately ten micrometers (10 $\mu$m) are formed by the laser system 10 and have an average energy of approximately five microjoules (5 $\mu$J), rendering each focal point suitable for photoalteration of stromal tissue. Further, in the preferred embodiment of the present invention, the six focal points (60a and 60c–g) are arranged in a circle having a diameter 64 of approximately one hundred micrometers (100 $\mu$m), ensuring that each focal point 60a–g is spaced from the remaining focal points 60a–g by a distance 66 of at least approximately twenty micrometers (20 $\mu$m). This spacing assures adequate heat dissipation during photoalteration, thereby preventing heat damage to non-target tissue.

Figure 7:
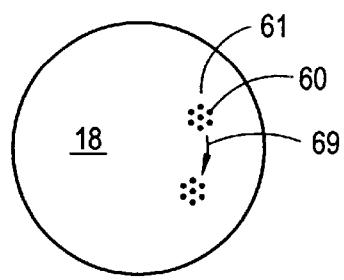
FIG. 7 is an enlarged plan view of a portion of the cornea of an eye showing the movement of a cluster of focal points during a surgical procedure in accordance with the present invention.
Figure 8:
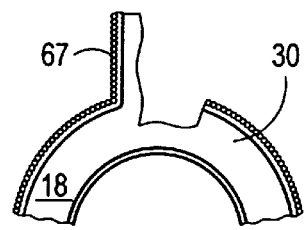
FIG. 8 is a cross sectional view as in FIG. 3, after a corneal flap has been incised using a laser system in accordance with the present invention, and lifted.

Referring now to FIG. 4, it can be seen that a scanner 68 is preferably interposed between relay lens 54 and relay lens 56. For the present invention, any scanner known in the pertinent art for controlling the movement of a plurality of laser beams can be used. Cross referencing now to FIGS. 4 and 7, it can be seen that the scanner 68 is provided to move the cluster 61 of focal points 60 through the cornea 18 (such as in the direction of arrow 69 in FIG. 7). Preferably, the cluster 61 is scanned at a rate such that the cluster 61 is positioned at a location requiring photoalteration for approximately $\frac{1}{4000}^{th}$ of a second (for a 4 kHz laser source). As such, approximately one pulse of energy will be focused at each focal point 60, for each location that is photoaltered. For example, for the creation of a ten millimeter (10 mm) flap 67 as shown in FIG. 8, approximately 200,000 points in the stroma 30 require photoalteration. For a cluster 61 having seven focal points 60, approximately 30,000 locations require photoalteration. Thus, for this example, the scanner 68 is configured to scan the ten millimeter (10 mm) area in approximately seven to eight seconds. Alternatively, the cluster 61 of focal points 60 can be scanned within the stroma 30 to photoalter a volume of stromal tissue (such as volume 72 shown in FIG. 3) to effect a refractive change in the cornea 18.

Figure 9:
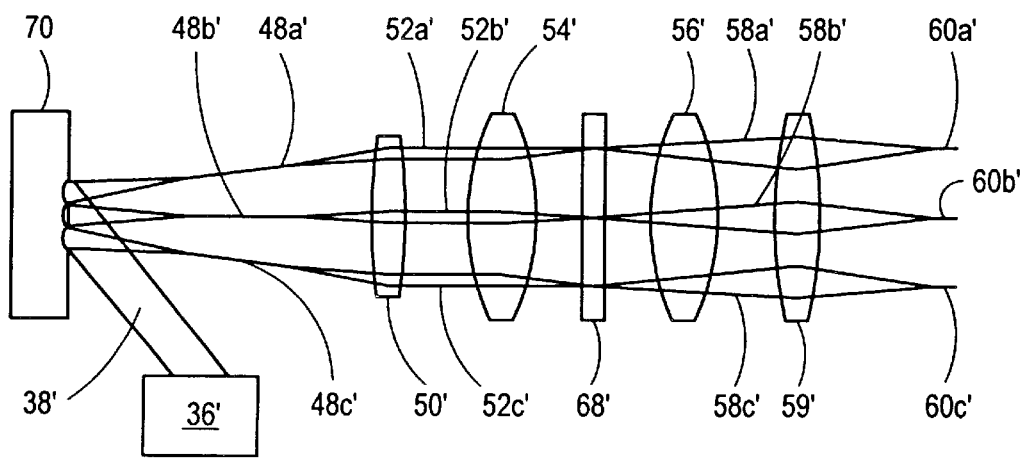
FIG. 9 is a schematic diagram of another embodiment of a laser system in accordance with the present invention having an active mirror for producing a plurality of diverging beams.

FIG. 9 shows another embodiment of a laser system 10' in accordance with the present invention. For clarity, the prime (') has been used to denote elements in FIG. 9 that are similar or identical in nature to like-numbered elements in the embodiment shown in FIG. 4. As shown in FIG. 9, a laser source 36', as described above is used to direct a pulsed laser beam 38' to an active mirror 70. Preferably, an active mirror 70 having approximately 40,000 active facets is used. As shown, the active mirror 70 is configured to reflect the pulsed laser beam 38' into seven, spaced apart diverging beams, of which three (48a'–48c') are shown in FIG. 9. It is to be appreciated by those skilled in the art that one or more optical prisms (not shown) can be substituted in place of the active mirror 70 to partition the pulsed laser beam 38' into diverging beams.

Referring still to FIG. 9, from the active mirror 70, the diverging beams 48a'–48c' are directed to a collimating lens 50' to place the seven beams onto parallel beam paths. Next, the collimated beams 52a'–52c' are directed through relay lens 54' and relay lens 56' for magnification. From the relay lenses 54', 56', the magnified beams 58a'–58c' are directed to a focusing lens 59' to focus each of the magnified beams 58a'–58c' to a separate focal point 60a'–60c'. Scanner 68' is provided to simultaneously move all the focal points 60a'–60c' during the procedure.

While the particular laser beam delivery system with multiple focal points as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A laser system for creating a plurality of focal points for use in an ocular laser procedure, said system comprising:
   a means for creating a pulsed laser beam;
   an active mirror having approximately 40,000 active facets for partitioning said pulsed laser beam to produce a plurality of beams;
   a means for focusing said plurality of beams to produce a plurality of focal points arranged as a cluster; and
   a means for scanning said cluster to simultaneously move said plurality of focal points in said cluster within the eye during the procedure.

2. A laser system as recited in claim 1 further comprising:
   a means for collimating said plurality of beams to produce a plurality of collimated beams; and
   a means for magnifying said plurality of collimated beams to produce a plurality of magnified beams, said plurality of magnified beams being for focusing into said plurality of focal points.

3. A laser system as recited in claim 1 wherein said creating means is configured to create a pulsed laser beam having an average energy per pulse of approximately 60 $\mu$J and each said focal point of said plurality of focal points has an average energy per pulse of approximately 5 $\mu$J.

4. A laser system as recited in claim 3 wherein said creating means is configured to create a pulsed laser beam having a pulse frequency of approximately 4 kHz.

5. A laser system as recited in claim 1 wherein said plurality of focal points is seven focal points.

6. A laser system for photoalteration of stromal tissue in the cornea of patient, said laser system comprising:
   a means for creating a pulsed laser beam, said laser beam having a pulse frequency of approximately 4 kHz and an average pulse energy of approximately 60 $\mu$J;
   a means for partitioning said pulsed laser beam to produce a plurality of beams;
   a means for focusing said plurality of beams to produce a plurality of focal points, with each said focal point having an average energy per pulse of approximately 5 $\mu$J; and
   a means for scanning said plurality of focal points to simultaneously move each said focal point within the stroma to photoalter a predetermined volume of stromal tissue.

7. A laser system as recited in claim 6 wherein each said focal point is separated from the nearest said focal point by a distance of at least 25 μm.

8. A laser system as recited in claim 6 wherein said plurality of focal points is seven focal points and said focal points are arranged with six focal points uniformly distributed about a circle surrounding a seventh focal point positioned at the center of said circle.

9. A laser system as recited in claim 6 wherein said partitioning means and said focusing means comprise:

an active mirror to produce a plurality of diverging beams from said pulsed laser beam;

a collimating lens for collimating said plurality of diverging beams to produce a plurality of collimated beams;

a pair of relay lenses to magnifying said plurality of collimated beams to produce a plurality of magnified beams; and a cutting lens for focusing said plurality of magnified beams to produce a plurality of focal points.

10. A laser system as recited in claim 9 wherein said active mirror has approximately 40,000 active facets.

11. A laser system as recited in claim 6 herein said partitioning means and said focusing means comprise:

a lenslet array to produce a plurality of beams from said pulsed laser beam;

a field lens to diverge said plurality of beams and produce a plurality of diverging beams;

a collimating lens for collimating said plurality of diverging beams to produce a plurality of collimated beams;

a pair of relay lenses to magnify said plurality of collimated beams to produce a plurality of magnified beams; and a cutting lens for focusing said plurality of magnified beams to produce a plurality of focal points.

12. A method for subsurface photoalternation of tissue, said method comprising:

generating a pulsed laser beam;

partitioning said pulsed laser beam to produce a plurality of spaced apart beams;

focusing each said beam of said plurality of spaced apart beams to a plurality of subsurface focal points to photoalter subsurface tissue at each said focal point; and scanning said plurality of focal points to simultaneously move said plurality of focal points within the tissue during the procedure.

13. A method as recited in claim 12 further comprising the step of using a field lens to diverge said plurality of spaced apart beams and produce a plurality of diverging beams prior to said focusing step.

14. A method as recited in claim 12 further comprising the step of using a collimating lens to collimate said plurality of diverging beams and produce a plurality of collimated beams prior to said focusing step.

15. A method as recited in claim 14 further comprising the step of using a pair of relay lenses to magnify said plurality of collimated beams prior to said focusing step.

16. A method as recited in claim 15 wherein said scanning step is accomplished to create a corneal flap.

17. A method as recited in claim 15 wherein said scanning step is accomplished to alter the refractive properties of the cornea.

* * * * *